United States Patent [19]

Keana et al.

[11] Patent Number: 5,308,869
[45] Date of Patent: May 3, 1994

[54] SUBSTITUTED AMIDINES HAVING HIGH BINDING TO THE SIGMA RECEPTOR AND THE USE THEREOF

[75] Inventors: John F. W. Keana, Eugene; Eckard Weber, Portland, both of Oreg.

[73] Assignee: State of Oregon, acting by and through the Oregon State Board of Higher Education, acting**, Portland, Oreg.

[21] Appl. No.: 860,571

[22] Filed: Mar. 30, 1992

Related U.S. Application Data

[63] Continuation of Ser. No. 574,672, Aug. 30, 1990, abandoned.

[51] Int. Cl.$^5$ ............................................. A01N 37/52
[52] U.S. Cl. ..................................... 514/637; 514/150; 514/524; 514/631; 534/676; 534/679; 534/683; 534/735; 534/738; 558/17; 558/418; 558/419; 558/422; 558/423; 558/425; 558/426; 558/428; 564/225; 564/244; 564/245; 564/246; 564/247
[58] Field of Search ..................... 564/225, 244, 245; 514/524, 631

[56] References Cited

U.S. PATENT DOCUMENTS

| | | | |
|---|---|---|---|
| 2,004,994 | 6/1935 | Lee | 560/35 |
| 3,632,593 | 1/1972 | Gautier et al. | 260/296 R |
| 3,968,211 | 7/1976 | DuCharme | 424/248 |
| 3,972,931 | 8/1976 | McCarthy, Jr. | 260/564 R |
| 3,983,250 | 9/1976 | Abdallah et al. | 424/326 |
| 3,987,158 | 10/1976 | Hodson | 424/9 |
| 3,988,364 | 10/1976 | Kuroda et al. | 562/597 |
| 4,052,455 | 10/1977 | Matier et al. | 260/562 R |
| 4,130,663 | 12/1978 | Matier et al. | 424/326 |
| 4,183,957 | 1/1980 | Pawloski | 514/637 |
| 4,347,382 | 8/1982 | Scharver | 564/183 |
| 4,795,627 | 1/1989 | Fisher et al. | 424/1.1 |

OTHER PUBLICATIONS

Desk, *Chem. Abstr.* 114:101290x (1990).
The International Search Report for the Corresponding International Application No. PCT/US91/06030 (1991).

*Primary Examiner*—Allen J. Robinson
*Assistant Examiner*—Brian M. Burn
*Attorney, Agent, or Firm*—David G. Conlin; Peter F. Corless

[57] ABSTRACT

N,N'-disubstituted-amidines, e.g., of the formula

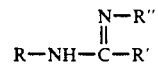

wherein R, R' and R" are substituted or unsubstituted hydrocarbon and/or heterocyclic groups.

Methods are provided for the treatment or prophylaxis of anxiety in an animal, for treating psychosis, and for treating hypertension by administering an effective amount of an N,N'-disubstituted amidine which, preferably, has a high affinity for the sigma receptor.

51 Claims, No Drawings

SUBSTITUTED AMIDINES HAVING HIGH BINDING TO THE SIGMA RECEPTOR AND THE USE THEREOF

STATEMENT AS TO RIGHTS TO INVENTIONS MADE UNDER FEDERALLY SPONSORED RESEARCH AND DEVELOPMENT

This invention was made with government support under Grant Nos. MH 42068 and MH 40303 awarded by the National Institutes of Health. The government has certain rights in the invention.

This application is a continuation of application Ser. No. 07/574,672, filed Aug. 30, 1990, now abandoned.

FIELD OF THE INVENTION

The invention is in the field of medicinal chemistry. In particular, the invention relates to substituted amidines which bind to the sigma receptor and pharmaceutical compositions thereof which are useful for the treatment of psychotic mental illness, hypertension and for the treatment or prevention of anxiety in animals.

BACKGROUND OF THE INVENTION

A wide variety of substituted amidines are disclosed in the patent literature. For example:

U.S. Pat. No. 3,903,163 (1975), discloses N,N'-disubstituted 2-naphthyleneacetamidines having activity as anti-depressants, anti-anxiety or calming agents. The N,N'-substituents are $C_1$-$C_3$ alkyl. See also U.S. Pat. No. 4,134,992 (1979).

U.S. Pat. No. 3,972,931 (1976), discloses N,N'-disubstituted benzamidines as antidepressants, anti-anxiety and calming agents. The benzene radical is substituted in the 3- and/or 4-position by a halogen and the N,N'-substituents are $C_1$-$C_3$ alkyl. See also U.S. Pat. No. 3,988,474 (1976).

U.S. Pat. No. 3,934,020 (1976), discloses N,N'-dialkyl-2-halophenylacetamidines as antidepressants and anti-anxiety agents. The benzene radical is substituted in the 3- and/or 4-position by halogen or $CF_3$ and the N,N'-substituents are $C_1$-$C_3$ alkyl. See also U.S. Pat. No. 3,983,250 (1976).

U.S. Pat. No. 2,221,280 (1938), discloses acetamidines which can be used to make alkylated or aralkylated amidines. These compounds reportedly can be used as textile agents, pesticides, bactericides and fungicides. The amidine starting compounds are preferably aryl amidines.

U.S. Pat. No. 596,797 (1897), discloses dialkoxyphenylamidines as local anesthetics.

U.S. Pat. No. 2,004,994 (1933), discloses diaryl acetamidines having utility as therapeutic agents. One aryl is substituted by a 2-ethoxy and a 5-phenyl group and the other aryl group is substituted in the 4-position with ethoxy or carbethoxy and the 3-position is optionally substituted by phenyl.

U.S. Pat. No. 3,632,593 (1972), discloses N-aryl-substituted aromatic amidines which are useful as analgesics, anti-inflammatory agents, neurosedative agents and hypotensive agents.

U.S. Pat. No. 4,503,076 (1985), discloses N-(2,6-dichlorophenyl)acetamidine as a vasodilator antihypertensive agent.

U.S. Pat. No. 3,906,044 (1975), discloses adamantylamidines and their use as antiviral agents. The adamantyl radical, which is optionally substituted by alkyl groups, can be directly linked to the carbon atom of the amidine or linked through a methylene linkage.

See also U.S. Pat. Nos. 4,183,957 (1980), 3,284,289 (1966), 3,678,109 (1972), 3,689,675 (1972), 3,729,565 (1973), 3,888,927 (1975).

U.S. Pat. No. 4,709,094 (1987), discloses N,N'-disubstituted guanidine derivatives which exhibit high binding activity with respect to the sigma receptor having the formula (I):

wherein R and R' are an alkyl group of at least 4 carbon atoms, a cycloalkyl group of 3–12 carbon atoms, or carbocyclic or aryl, of at least 6 carbon atoms.

Two of the novel N,N'-disubstituted guanidines disclosed therein are also claimed therein viz., 1,3-di-(4-halo-2-methylphenyl)-guanidine and 1,3-di-(4-[$^3$H]-(2-methylphenyl)-guanidine.

Also claimed therein is a method of determining the relationship of abnormal psychotic-like behavior in a mammal displaying such behavior to sigma receptor system dysfunction, which comprises administering to the mammal displaying such behavior a water-soluble N,N'-disubstituted-guanidine which displaces in vitro N,N'-di-(4-[$^3$H]-2-methylphenyl)-guanidine bound to mammalian brain membrane, in an amount effective to alter the sigma brain receptor-modulated mental activity of the mammal and a method of treating a human being suffering from a psychotic mental illness associated with hallucinations, which comprises administering thereto a water-soluble N,N'-di-substituted guanidine which is an antagonist to the sigma receptor binding activity of a hallucinogenic benzomorphan, in an amount effective to ameliorate the hallucinations.

In U.S. Pat. No. 4,709,094 is further disclosed a method of determining the sigma brain receptor binding activity of an organic compound which comprises the steps of a) contacting in an aqueous medium a known amount of isolated mammalian brain membrane which has sigma receptor-like binding activity, with a mixture of (i) a tritium labeled N,N'-disubstituted guanidine which selectively binds sigma brain receptors, in a known amount capable of being bound to the sigma receptors of that brain membrane; and (ii) varying known amounts of a water soluble organic compound to be assayed for sigma receptor binding activity; b) separating the brain membrane from the tritium labeled compound which is not bound to the brain membrane in step a); and c) determining, from the molar relationship of the proportion of bound tritium-labeled compound which is separated in step b) to the molar amount of the organic compound employed in step a), the sigma receptor binding activity of that organic compound.

Certain benzomorphan opiates, such as N-allyl-normetazocine (SKF 10,047) and cyclazocine, in addition to analgesia, cause hallucinations, depersonalization, drunkenness and other psychotomimetic effects in man. In monkeys, dogs and rodents the psychotomimetic opiates cause behavioral and autonomic effects that are unlike those observed with administration of classical opiates such as morphine or the opioid peptides. Specific sigma "opioid" receptors in the brain are believed to mediate such atypical effects. Martin et al., *J. Pharmacol. Exp. Ther.* 197:517–532 (1976). It is believed that the sigma receptors also mediate some of the psychotomimetic effects of phencyclidine [PCP, angel dust], or alternatively, that psychotomimetic opiates act at specific PCP receptors. Zukin, R. S. et al., *Mol. Pharmacol.* 20:246-254 (1981); Shannon, H. E., *J. Pharmacol. Exp Ther.* 225:144-152 (1983); White, J. M. et al., *Psychopharmacology* 80:1-9 (1983); and Zukin et al., *J. Neurochem.* 46:1032-1041 (1986). PCP is a drug of abuse that causes a behavioral syndrome in man similar to that which is observed in schizophrenic psychosis. Aniline, O. et al., *CRC Critical Rev. Toxicol.* 10:145-177 (1982). Because of the potent psychotomimetic effects of sigma opiates and PCP, it is believed that sigma (and/or PCP) receptors play a role in mental illness, particularly schizophrenia.

A systematic investigation of the role of sigma receptors in normal and abnormal brain function has been hindered by a lack of specific sigma receptor binding assays and bioassays. Development of such specific assays requires well-characterized, highly selective and potent sigma receptor ligands. Recent studies have shown that brain membrane receptors can be labeled in vitro with (±)[$^3$H]SKF 10,047, Su, T. P., *J. Pharmacol. Exp. Ther.* 223:284-290 (1982); (+)[$^3$H]SKF 10,047, Tam, S. W. et al., *Proc. Natl. Acad. Sci. U.S.A.* 81:5618-5621 (1984); Martin et al., *J. Pharmacol. Exp. Ther.* 231:539-544 (1984); and Mickelson, M. M. et al., *Res. Commun. Chem. Pathol. Pharmacol.* 47:255-263 (1985), although not selectively, Gundlach et al., *Eur. J. Pharmacol.* 113:465-466 (1985); and Largent, B. L. et al., *J. Pharmacol. Exp. Ther. ZLB:* 739-748 (1986), and with (+)[$^3$H]3-(3-hydroxyphenyl)-N-(1-propyl)-piperidine ((+)[$^3$H]3-PPP), Largent et al., *Proc. Natl. Acad. Sci. U.S.A.* 81:4983-4987 (1984), which is apparently more selective for sigma receptors than the others.

After the initial in vitro studies by Martin et al., (1976) supra, Keats and Telford (Keats, A. S. et al., "Analgesics: Clinical Aspects." In *Molecular Modification in Drug Design*, R. F. Gould (ed.), Advances in Chemistry Series #45 Amer. Chem. Soc., Wash. D.C. (1964)), and Haertzen (Haertzen, C. A. Cyclazocine and Nalorphine on the Addiction Research Center Inventory (ARCI), *Psychopharmacologia* (Berl.) 18:366-377 (1970)), numerous investigators set out to biochemically characterize the different opiate receptors (mu receptors, kappa receptors and sigma receptors) in vitro.

The first evidence for the existence of a separate sigma receptor in test tube experiments was provided by Su (1982) supra in a paper describing an etorphine-inaccessible binding site in guinea pig brain membranes which was apparently selectively labeled by tritium-labeled SKF-10,047. To overcome the fact that SKF-10,047 could label multiple opioid receptors in the brain, Su performed his receptor binding assay using tritium labeled SKF-10,047 in the presence of excess unlabeled etorphine. Etorphine is a very strong opiate agonist drug which is known to bind to delta receptors, mu receptors and kappa receptors with almost equal potency. Su used etorphine to saturate all mu, kappa and delta receptors in a brain membrane preparation and then added tritium labeled SKF-10,047. This enabled him to detect a sigma binding site that was apparently different from mu, kappa and delta receptors.

A major breakthrough in identifying the sigma receptor as a separate entity occurred when Tam et al. (1984), supra, demonstrated that the previous problems in selectively labeling the sigma receptor were caused by the fact that in all previous experiments a racemic SKF-10,047 preparation was used. Tam showed that using a tritium labeled (+)-SKF-10,047 isomer one could selectively label a sigma receptor that was different from the mu, delta and kappa opioid receptors. On the other hand, Tam showed that (−)-SKF-10,047 apparently labeled the mu and kappa receptors but not the sigma receptors. Tam, S. W., *Eur. J. Pharm.* 109:33–41 (1985). This finding has now been confirmed. (Martin et al., 1984, supra). Moreover, there is evidence from behavioral experiments, Khazan et al., *Neuropharm.* 23:983-987 (1984); Brady et al., *Science* 215:178-180 (1981), that it is the (+)-SKF-10,047 isomer that is solely responsible for the psychotomimetic effects of SKF-10,047.

One of the most important findings of the biochemical characterization of the sigma receptor has been that this receptor binds all synthetic opiate drugs that are known to have hallucinogenic and psychotomimetic effects. Opiates that do not have psychotomimetic effects in vivo do not bind to this receptor. Most importantly, it has been shown that besides hallucinogenic opiate drugs, the sigma receptor also binds many antipsychotic drugs that are used clinically to treat hallucinations in schizophrenic patients. (Tam and Cook, 1984). The initial observations with regard to antipsychotic drug binding to the sigma receptor (Su, 1982) were subsequently extensively confirmed and extended by Tam et al. (1984), supra, also showed that when one used radioactively labeled haloperidol, one of the most potent antipsychotic drugs that is used clinically, about half of the binding sites in brain membrane preparations are actually sigma receptors whereas the other half of the binding sites are apparently dopamine receptors. It has long been known that most antipsychotic drugs are also dopamine receptor antagonists. Previously, the beneficial actions of antipsychotic drugs in psychotic patients have been attributed to the dopamine receptor-blocking effect of these drugs. It is clear from the work by Tam, however, that numerous clinically used antipsychotic drugs also bind to the sigma site. All antipsychotic drugs that bind to the sigma receptor may in part cause the beneficial effect of alleviating hallucinations through the sigma receptor. Taken together all these observations suggest the sigma receptor as a prime candidate to be involved in the pathogenesis of mental illness, particularly schizophrenia in which hallucinations are a major clinical symptom.

Deutsch, S. I. et al. (*Clinical Neuropharmacology*, Vol. 11, No. 2, pp. 105-119 (1988)) provided a review of the literature which implicates the sigma receptor site in psychosis and anti-drug efficacy. According to Deutsch et al., certain benzomorphans which possess analgesic potency in humans are also associated with a high incidence of psychotomimetic effects. It has now been concluded that the analgesic action is associated with the levorotatory isomers of racemic mixtures of the benzomorphans, while the psychotomimetic effects are attributable to the dextrorotatory isomers in the racemic mixtures. See Haertzen, C. A., *Psychopharmacologia* 18:366-77 (1970), and Manallack, D. T. et al., *Pharmacol. Sci.* 7:448-51 (1986). Coupled with the fact that many of the in vivo effects of these dextrorotatory enantiomers and the binding of dextrorotatory tritiated SKF-10,047 are not antagonized by naloxone or naltrexone, these data strongly support the concept that the psychotomimetic effects of the dextrorotatory enantiomers are associated with the sigma receptor binding site.

Further, Su, T. P. et al. (*Life Sci.* 38:2199-210 (1986)), and Contreras, P. C. et al. (*Synapse* 1:57-61 (1987)), have proposed the existence of endogenous ligands for the sigma receptor, suggesting that the dysregulation of the synthesis, release, or degradation of these natural ligands may be a naturally occurring mechanism of psychosis. Accordingly, sigma receptor antagonism provides the potential for an effective antipsychotic therapeutic treatment. See Ferris, R. M. et al., *Life Sci.* 38-2329-37 (1986), and Su, T. P., *Neurosci. Let.* 71:224-8 (1986).

As further evidence of the role of the sigma receptor in psychosis, the substituted carbazole cis-9-[3-(3,5-dimethyl-1-piperazinyl)-propyl]carbazole dihydrochloride (rimcazole) was identified as a potential antipsychotic agent based on its ability to antagonize apomorphine-induced mesolimbic behaviors selectively without altering the intensity of stereotypic behaviors. Further, the compound does not accelerate the rate of dopamine synthesis and does not affect dopamine-stimulated production of CAMP in homogenates of rat striatum and olfactory tubercle, thus establishing that rimcazole does not exert its action at the level of postsynaptic dopamine receptors in the mesolimbic area.

Rimcazole is able to competitively inhibit the specific binding of dextrorotatory tritiated SKF-10,047, the prototype sigma receptor agonist, suggesting that rimcazole acts at the sigma receptor site. Rimcazole, therefore, shows potential antipsychotic activity in humans, without extrapyramidal effects, pharmacological behavior which is consistent with its role as a competitive antagonist of the sigma-receptor.

Another compound, BMY 14802, has demonstrated many properties in preclinical behavioral tests which suggest its efficacy as a potential antipsychotic agent which is devoid of extrapyramidal side effects. The compound (1) did not cause catalepsy in rats; (2) does not inhibit the binding of [$^3$H]spiperone to the $D_2$ class of striatal dopamine receptors in rats; (3) did not increase the maximal density of the ($^3$H]spiperone-labeled $D_2$ site in striatum even following chronic administration (20 days) to rats; (4) does not appear to interact with the $D_1$ subclass of dopamine receptors; and (5) does not inhibit dopamine-stimulated CAMP production or the binding of [$^3$H)SCH 23390 in vitro. These data suggest that BMY 14802 has a low potential for production of tardive dyskinesia and further suggests that the antipsychotic effects would be mediated by a nondopaminergic site. Further, BMY 14802 binds with relatively high affinity to the sigma receptor, with the binding being stereoselective (the dextrorotatory enantiomer being 10 times more potent at inhibiting binding than the levorotatory enantiomer). BMY 14802 does not bind to the adrenergic, muscarinic, cholinergic, or histaminergic sites, suggesting that the compound would not be associated with unpleasant sedative and autonomic side effects.

Accordingly, compounds which bind selectively to the sigma receptor site and which antagonize this site may be expected to be useful antipsychotic drugs which are devoid of extrapyramidal effects.

The antipsychotic and anti-schizophrenia drugs that are currently in use have very strong side effects that are mainly due to their action on dopamine receptors. The side effects often involve irreversible damage to the extrapyramidal nervous system which controls movement functions of the brain. Patients under long term antischizophrenic drug treatment often develop a syndrome that involves permanent damage of their ability to control coordinated movement.

The foregoing studies have shown that the sigma binding site has the characteristics of 1) stereo-selectivity towards dextrorotatory benzomorphan opiates and insensitivity for naloxone; 2) high affinity for haloperidol and moderate to high affinity for phenothiazine antipsychotic drugs which are also known to be potent dopamine receptor blockers; and 3) insensitivity for dopamine and apomorphine. This intriguing drug selectivity profile calls for a thorough analysis of the role of sigma receptors in normal and abnormal brain function. In order to do so, it is essential that a spectrum of highly selective and potent sigma receptor active compounds be available.

Fear, or apprehension, is characterized by the anticipation of a known danger or event. In contrast, neurotic anxiety is characterized by an apprehension with no known cause, or a maladaptive response to a trivial danger. In recent years, generalized anxiety disorder (GAD) has been characterized by psychiatrists as being chronic (continually present for at least 1 month) and exemplified by three of four psychomotor symptoms: motor tension, autonomic hyperactivity, apprehensive expectation, and vigilance and scanning. Before this characterization was adopted, clinical trials of anxiolytic agents in the United States occurred in patients which were described variously as suffering from anxiety neurosis, anxiety with associated depression, and other such terms. Anxiety disorders affect 2-3% of the general population (the 67 million prescriptions written in 1977 for just two popular anxiolytics confirm this projected incidence). The popularity of anxiolytics attests to their ability to ameliorate the debilitating symptoms of the disease. Taylor, D. P., *FASEB J.* 2: 2445-2452 (1988).

Historically, anxiety has been treated by agents including alcohol, opiates, and belladonna, which have a sedative component to their action. In the 20th century novel chemical entities were discovered which are safer for the treatment of anxiety including barbiturates, propanediol carbamates, and benzodiazepines. The pharmacological profiles of these drugs have suggested that their actions are mediated by receptors for γ-aminobutyric acid (GABA). Although the benzodiazepines present a safer alternative than meprobamate and phenobarbital, they also are sedatives. In addition, the benzodiazepines control convulsions and produce muscle relaxation, properties that are unneeded or undesirable in the treatment of anxiety. Furthermore, these drugs can interact with alcohol, with potentially disastrous consequences. Recently, it has been appreciated that the benzodiazepines produce habituation and possess a pronounced liability, for example, withdrawal symptoms after chronic use. The need for anxioselective drugs that are more selective, have fewer side effects, and present a profile consistent with safety during protracted treatment has resulted in a continuing search for such drugs. This search has led to the synthesis and evaluation of agents that possess no obvious homology with the benzodiazepines. Taylor et al., supra.

Buspirone (Buspar) was the first novel anxiolytic to be approved for clinical use in the United States since the benzodiazepines were introduced almost 30 years ago. The introduction of buspirone into clinical trials for the treatment of anxiety was a direct result of its efficacy in a predictive animal model for the disease—the taming of the aggressive response of rhesus monkeys to the introduction of foreign objects into their cages according to the protocol described by Tompkins, E. C. et al., *Res Commun. Psychol. Psychiatry Behav.*, 5:337-352 (1980). See Taylor et al., supra.

The preclinical screening of putative anxiolytics is dependent upon animal tests. Most of the laboratory data on new putative anxiolytics come from animal tests from two main classes. The first group of tests are based on conflict or conditioned fear. The second group of tests are based upon anxiety generated by novel situations. Although these tests differ in the way anxiety is produced, there has been surprising agreement amongst them in the classification of drugs as anxiolytic or anxiogenic. See File, S. E., *TINS* 10:461-463 (1987).

In two particular tests for anxiolytic activity, it is assumed that the anticipation of punishment causes a reduction in a response associated with the punishment. Conversely, anxiolytic agents that reduce anxiety result in an increased response rate. In the Geller-Seifter test, the rat receives food reward for pressing a lever, but also receives an electric foot shock, which has the effect of suppressing the response. This punished schedule alternates with an unpunished schedule wherein electric footshocks are not administered. During this unpunished schedule, lever-pressing is still rewarded. In the Vogel test, a rat is allowed to drink water, but also receives an electric shock through the water spout or the bars of the floor. In both the Vogel and Geller-Seifter tests, a measure of unpunished response is obtained in order to allow assessment of any non-specific stimulant or sedative drug effects or any changes in food or water intake. In both of these tests, benzodiazepines enhance the response rate in the punished periods, without increasing the rate of response in the absence of shock. While these tests are valid tests of anxiety, the only means of assessing them has been pharmacological. Taylor et al., supra.

A less widely used test utilizes punished locomotion, wherein a measure of unpunished crossing is obtained according to the rate at which a mouse crosses from one metal plate to another, wherein footshocks are administered whenever the mouse crosses. Although less widely utilized to test anxiolytic agents, this test has been able to detect drug-induced increases and decreases in anxiety by manipulating the shock level. File, S. E., *J. Neurosci Methods* 2:219-238 (1980).

The social interaction test of anxiety (File, supra; Jones, B. J. et al., *Br. J. Pharmacol.* 93: 985-993 (1988) exploits the uncertainty and anxiety generated by placing rats in an unfamiliar environment and in bright light. The dependent variable is the time that pairs of male rats spend in active social interaction (90% of the behaviors are investigatory in nature). Both the familiarity and the light level of the test arena may be manipulated. Undrugged rats show the highest level of social interaction when the test arena is familiar and is lit by low light. Social interaction declines if the arena is unfamiliar to the rats or is lit by bright light. Anxiolytic agents prevent this decline. The overall level of motor activity may also be measured to allow detection of drug effects specific to social behaviors.

The social interaction test of anxiety is one of the few animal tests of anxiety that has been validated behaviorally. Other behavioral measures indicative of anxiety and stress (e.g. defecation, self-grooming and displacement activities) were correlated with the reductions in social interaction; and other causes of response change (e.g. exploration of the environment, odor changes) were excluded. In order to validate the test physiologically, ACTH and corticosterone levels and changes in hypothalamic noradrenaline also were measured. File, *TINS* 10: 461-463 (1987).

Another test of anxiety that exploits the anxiety generated by a novel situation is the elevated plus maze. In this test, the anxiety is generated by placing the animals on an elevated open arm. Height, rather than the light level, is responsible for generating behavioral and physiological changes. The apparatus is in the shape of a plus with two open and two enclosed arms. The rat has free access to all arms on the apparatus. Anxiolytic activity may be measured by the percentage increase in the time that the test animal spends on the open arms and the number of entries onto the open arms. This test has also been validated behaviorally and physiologically.

Other agents which have been determined to have anxiolytic activity include the carbazole derivative 9-[3-(3,5-cis-dimethylpiperazino)-propyl]carbazole having the Formula (II):

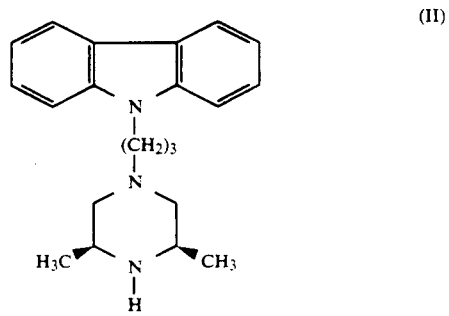

and pharmaceutical compositions thereof. See U.S. Pat. No. 4,400,383 (1983).

Serotonin receptor antagonists are also known to be useful for the treatment of anxiety. See Kahn, R. S. et al., *J. Affective Disord*, 8:197-200 (1987); Westenberg, H. G. M. et al., *Psychopharmacol. Bull.* 23:146-149 (1987).

SUMMARY OF THE INVENTION

The invention relates to a novel class of N,N'-disubstituted amidines which are radioactively tagged and which are useful for assaying in vitro the sigma receptor binding activity of organic compounds.

The invention also relates to novel N,N'-disubstituted amidines which bind to sigma receptor sites, especially those which do so with high affinity and/or selectively. The substituted amidines of the invention have the Formula (III):

wherein R, R' and R" are hydrogen, an alkyl group of 1-8 carbon atoms, a cycloalkyl group of at least 3 carbon atoms, a carbocyclic aryl group of at least 6 carbon atoms, alkaryl or aralkyl of at least 6 carbon atoms and containing 1-3 separate or fused rings, or a heterocyclic ring, wherein R' additionally can be $C_{2-6}$ alkenyl, phenylsulfonyl or $C_{1-6}$ alkylsulfonyl; and wherein each of R, R' and R" may be substituted in 1-3 positions, or wherein R and R" together with the amidine group to which they are attached form a saturated or unsaturated cyclic ring containing at least 2 carbon atoms exclusive of the amidine carbon atom, and wherein said cyclic ring may be substituted with one or more alkyl groups of 1-6 carbon atoms, carbocyclic aryl groups of at least 6 carbon atoms, cycloalkyl groups of 3-12 carbon atoms, or 1-2 fused aromatic rings. Preferably, R' is $C_1-C_6$ alkyl, $C_2-C_6$ alkenyl, phenyl, trifluoromethyl, phenylsulfonyl, or $C_1-C_6$ alkylsulfonyl.

Preferably, said N,N'-disubstituted amidine exhibits a high affinity for the sigma receptor and/or exhibit anxiolytic, antipsychotic and/or antihypertensive activity in an animal as demonstrated by, for example, an animal model.

In particular, the invention relates to N,N'-disubstituted amidines of the Formula (III):

(III)

wherein R and R'' each are adamantyl, cyclohexyl, a monocyclic carbocyclic aryl of at least 6 carbon atoms, norbornyl or isobornyl; and R' is hydrogen, $C_1-C_6$ alkyl, $C_2-C_6$ alkenyl, phenyl, trifluoromethyl, phenylsulfonyl, or $C_1-C_6$ alkylsulfonyl. Preferably, R' is methyl, ethyl or phenyl.

The invention also relates to substituted amidines having the Formula (IV):

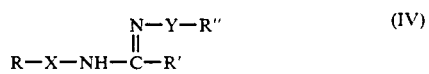
(IV)

wherein X and Y are independently a branched or straight chain $C_1-C_8$ alkylene or a branched or straight chain $C_2-C_8$ unsaturated alkylene; R and R'' are independently a cycloalkyl group of at least 3 carbon atoms, a carbocyclic aryl group of at least 6 carbon atoms, aralkyl of at least 6 carbon atoms and containing 1-3 separate or fused rings, or a heterocyclic ring, and wherein each of R and R'' may be substituted in 1-3 positions, or wherein R and R'' form a bond to give a saturated or unsaturated cyclic ring containing at least 2 carbon atoms exclusive of the amidine carbon atom, wherein said cyclic ring may be substituted with one or more alkyl groups of 1-6 carbon atoms, carbocyclic aryl groups of at least 6 carbon atoms, cycloalkyl groups of 3-12 carbon atoms, or 1-2 fused aromatic rings; and R' is hydrogen, $C_1-C_6$ alkyl, $C_2-C_6$ alkenyl, phenyl, trifluoromethyl, phenylsulfonyl, or $C_1-C_6$ alkylsulfonyl. Preferably, said N,N'-disubstituted amidine exhibits a high affinity for the sigma receptor.

The invention also relates to tritiated derivatives of the above-listed N,N'-disubstituted amidines wherein at least one of the ring carbon atoms of R, R' and R'' bears at least one tritium atom The invention also relates to pharmaceutical compositions comprising the aforesaid N,N'-disubstituted amidines, especially those having high affinity for the sigma receptor. In particular, the invention relates to pharmaceutical compositions, in unit dosage form and adapted for systemic administration to a human being, which comprises, per unit dosage, an amount effective to alter the sigma brain receptor-modulated activity of a human being displaying psychotic behavior or suffering from chronic depression, of an N,N'-disubstituted amidine in its water-soluble protonated form which displaces in vitro N,N'-di-(4-[$^3$H]-2-methylphenyl)-guanidine bound to isolated mammalian brain membrane.

The invention also relates to a method for determining the sigma receptor binding activity of organic compounds which comprises the steps of:

a) contacting in an aqueous medium a known amount of isolated mammalian brain membrane which has sigma receptor-type binding activity, with a mixture of (i) a tritium-labeled N,N'-disubstituted amidine which selectively binds sigma brain receptors, in a known amount capable of being bound to the sigma receptors of that brain membrane; and (ii) varying known amounts of a water soluble organic compound to be assayed for sigma receptor binding activity;

b) separating the brain membrane from the tritium labeled compound which is not bound to the brain membrane in step a);

c) determining, from the molar relationship of the proportion of bound tritium labeled compound which is separated in step b) to the molar amount of the organic compound employed in step a), the sigma receptor binding activity of that organic compound.

The invention also relates to a method for determining the relationship of abnormal psychotic-like behavior in a mammal displaying such behavior to sigma receptor system dysfunction by administering an N,N'-disubstituted amidine to a mammal in an amount effective to alter the sigma brain activity of the mammal. In particular, the invention relates to a method of determining the relationship of abnormal psychotic-like behavior in a mammal displaying such behavior to sigma receptor dysfunction, by administering thereto a sigma brain receptor-modulating amount of a water-soluble N,N'-disubstituted amidine which displaces in vitro N,N'-di-(4-[$^3$H]-2-methylphenyl)-guanidine bound to mammalian brain membrane, effective to alter the sigma brain receptor-modulated mental activity of that mammal.

The invention also relates to a method for treating abnormal psychotic-like behavior in mammals by administering the N,N'-di-substituted amidine compounds of the invention and pharmacological compositions thereof which are efficacious in the treatment of such abnormal psychotic-like behavior. In particular, the invention relates to a method of treating a human being suffering from chronic depression or a psychotic mental illness associated with hallucinations, e.g., schizophrenia, which comprises administering thereto a water soluble N,N'-disubstituted amidine which is an antagonist to the sigma receptor binding activity of a hallucinogenic benzomorphan, and/or which displaces in vitro N,N'-di-(4-[$^3$H]-2-methylphenyl)-guanidine bound to mammalian brain membrane, preferably a compound of Formulae (III) or (IV), in an amount effective to ameliorate the depression or hallucinations, respectively.

The invention also relates to methods for treating hypertension by administering the N,N'-disubstituted amidines of the invention or pharmaceutical compositions thereof.

The invention also relates to the discovery that certain substituted amidines having high binding to the sigma receptor are also potent anxiolytics and, at the same time may be substantially nonsedative. Therefore, these N,N'-disubstituted amidines are useful for the treatment or prophylaxis of anxiety in animals, i.e., humans. Therefore, the invention also relates to methods for the treatment or prophylaxis of anxiety in an individual susceptible to anxiety by administrating an anxiolytic amount of an N,N'-disubstituted amidine of the invention which exhibits a high affinity for the sigma receptor.

Certain amidines of the invention having selective sigma receptor binding may be of particular value in reducing or eliminating the undesirable extrapyramidal side effects associated with present antipsychotic medications.

DESCRIPTION OF THE PREFERRED EMBODIMENTS

The present inventors have discovered that the disubstituted amidines of this invention have sigma receptor binding activity, as evidenced by their ability to displace [$^3$H]DTG from guinea pig brain membrane binding sites. Availability of the selective sigma ligands of this invention facilitates characterization of sigma receptors in vivo and in vitro.

The preferred N,N'-disubstituted amidines of this invention are those of the Formula (III):

wherein R and R" each are an alkyl group of 1-8 carbon atoms, a cycloalkyl group of at least 3 carbon atoms, carbocyclic aryl groups of at least 6 carbon atoms, alkaryl or aralkyl groups of at least 6 carbon atoms and containing 1-3 separate or fused rings, or a heterocyclic ring. For example, R and R", which can be the same or different, are preferably a straight chain alkyl and more preferably a 4 to 8 carbon atom alkyl group, for example, butyl, isobutyl, tert-butyl, amyl, hexyl, and octyl; a cycloalkyl of 3 to 12 carbon atoms, e.g., cyclopropyl, cyclobutyl, cyclopentyl, cyclohexyl, cycloheptyl, 1,4-methylene-cyclohexanyl, adamantyl, cyclopentylmethyl, cyclohexylmethyl, 1- or 2-cyclohexylethyl, or 1-, 2- or 3-cyclohexylpropyl, carbocyclic aryl, alkaryl or aralkyl, e.g., of up to 18 carbon atoms and containing 1-3 separate or fused aromatic rings, e.g., phenyl, benzyl, 1- and 2-phenylethyl, 1-, 2-, or 3-phenylpropyl, o-, m- or p-tolyl, m,m'-dimethylphenyl, o-, m- or p-ethylphenyl, m,m'-diethylphenyl, m-pethyl-m'-ethylphenyl and o-propylphenyl, naphthyl, 2-naphthyl, bipheny), or a beterocycle, e.g., 2- and 4-pyridyl, pyrrolyl especially 2- and 3-N-methylpyrrolyl, 2- and 3-furanyl, 2- and 3-thiophenyl, 2- and 3-benzofuranyl, 2-benzoxazolyl, pyrazinyl, pyrimidyl, 2-, 4- and 5- thiazolyl, 2-, 4- and 5- oxazolyl, 2-, 4- and 5-imidazolyl, 2- and 3- indolyl, and 2- and 4- benzothiazolyl; and R' is hydrogen, $C_1$–$C_6$ alkyl, $C_2$–$C_6$ alkenyl, phenyl, trifluoromethyl, phenylsulfonyl, or $C_1$–$C_6$ alkylsulfonyl.

Additionally, 1, 2, 3 or more substituents which do not adversely affect the activity of the N,N'-disubstituted amidine moiety may be present on any one or all of the R, R' and R" hydrocarbon groups thereof, e.g., alkyl of 1-8 carbon atoms, e.g., methyl, ethyl; hydroxyalkyl of 1-8 carbon atoms; halo, e.g., chloro, bromo, iodo, fluoro; hydroxy; nitro; azido; cyano; isothiocyanate; amino; lower-alkylamino; di-lower-alkylamino; trifluoromethyl; alkoxy of 1-8 carbon atoms, e.g., methoxy, ethoxy and propoxy; acyloxy, e.g., alkanoyloxy of 1-8 carbon atoms, e. g., acetoxy and benzoyl; amido, e.g., acetamido, N-ethylacetamido; carbamido, e.g., carbamyl, N-methylcarbamyl, N,N'-dimethylcarbamyl; etc.

Especially preferred are compounds of Formula III wherein R and R" each are phenyl groups, which need not necessarily be identical, substituted with one or more of the foregoing substituents, for example, in the o-, m- or p- position or the 2,2-, 2,4- or 3,5-position, when the phenyl group is disubstituted or R is as herein defined and R,' is adamantyl . In addition, R' of the especially preferred compounds is methyl. Specific examples are those wherein R and R" both are phenyl or p-tolyl; R is o-tolyl and R" is p-bromo-o-tolyl, p-CF$_3$-o-tolyl, p-iodo-o-tolyl, p-iodo-phenyl, p-azido-o-tolyl, cyclohexyl, adamantyl, norbornyl or isobornyl; and R is phenyl and R" is p-bromo-o-tolyl, p-iodo-o-tolyl, m-nitro-phenyl or p-iodo-phenyl.

Examples of N,N'-disubstituted amidines which may be used in the practice of the invention are N,N'-bis(4-bromo-2-tolyl)acetamidine, N,N'-bis(2-ethylphenyl)acetamidine, N,N'-bis(o-methylphenyl)acetamidine, N,N'-bis(adamantan-1-yl)acetamidine, N-(adamantan-1-yl)-N'-(o-methylphenyl)acetamidine, N-(o-methylphenyl)-N'-(cyclohexyl)acetamidine, N,N'-bis(3-ethylphenyl)acetamidine, N,N'-bis(2-isopropylphenyl)acetamidine, N-exonorbornyl-N'-(2-methylphenyl)acetamidine, N-(adamantan- 1-yl)-N'-(cyclohexyl)acetamidine, N,N'-bis(1-naphthyl)acetamidine, N-(o-tolyl)-N'-methylacetamidine, N-(1-naphthyl)-N'-(3-ethylphenyl)acetamidine, N-(1-naphthyl)-N'-(2-isopropylphenyl)acetamidine, N,N'-dibutylacetamidine, N,N'-diphenylacetamidine, N,N'-di-(2-methyl-4-iodophenyl)acetamidine, N-(2-methyl-4-azido-phenyl)-N'-(2-methylphenyl)acetamidine, N,N'-diadamantylacetamidine, N-(2-iodophenyl)-N'-(2-methyl-phenyl)acetamidine, N-(2-methyl-4-nitrophenyl)-N'-(2-methylphenyl)acetamidine, N,N'-di-(2,6-dimethylphenyl)acetamidine, N-(2,6-dimethylphenyl)-N'-(2-methylphenyl)acetamidine, N,N'-di(cyclohexyl)acetamidine, N-adamantyl-N'-phenylacetamidine, N,N'-di-(m-n-propylphenyl)acetamidine, N,N'-di-(1-tetralinyl)acetamidine, N-(o-tolyl)-N'-(o-xylyl)acetamidine, N,N'-di-(o-xylyl)acetamidine, N-(3,5-dimethyladamantan-1-yl)-N'-(o-tolyl)acetamidine, N-(3,5-dimethyladamantan-1-yl)-N'-(o-iodophenyl)acetamidine, N-(1-adamantyl)-N'-(o-nitrophenyl)acetamidine, N,N'-di-((±)-endo-2-norbornyl)acetamidine, N-(exo-2-isobornyl)-N'-(o-iodophenyl)acetamidine, N,N'-di-(exo2-norbornyl)acetamidine, N-(exo-2-isobornyl)-N'-(o-tolyl)acetamidine, N-(o-iodophenyl)-N'-(t-butyl)acetamidine, N,N'-dibenzylacetamidine, N-(adamant-1-yl)-N'-(o-isopropylphenyl)acetamidine, N-(adamant-1-yl)-N'-(p-bromo-o-tolyl)acetamidine, N-(cyclohexyl)-N'-(p-bromo-o-tolyl)acetamidine, N-(adamant-2-yl)-N'-(o-iodophenyl)acetamidine, N-(adamant-1-yl)-N'-(o-iodophenyl)acetamidine, N-(adamantan-2-yl)-N'-(o-methylphenyl)acetamidine, N,N'-di-(endonorbornyl)acetamidine, N,N'-di-(exonorbornyl)acetamidine, N-endonorbornyl-N'-(o-tolyl)acetamidine, N-endonorbornyl-N'-(o-iodophenyl)acetamidine, N-exonorbornyl-N'-(o-tolyl)acetamidine, N-exonorbornyl-N'-(o-iodophenyl)acetamidine, and N-isobornyl-N'-(o-tolyl)acetamidine.

Among the compounds expected to have the highest sigma receptor binding activity are those compounds having Formula III wherein one of R and R" is adamantyl and the other is also adamantyl or o-substituted phenyl. Therefore, the preferred compounds of this invention include those wherein R and R" have those values, i.e., wherein the other of R and R" is a phenyl group substituted by, e.g., 1-4 carbon atoms, e.g., CH$_3$, C$_2$H$_5$, or i-C$_3$H$_7$, o-halophenyl wherein halo is Cl, Br, I or F, o-nitro-o-amino, o-carbo-lower alkoxy, e.g., COOCH$_3$, o-amino, e.g., —CONH$_2$, o-sulfato, o-carboxy, o-acyl, e.g., acetyl, o-CF$_3$, o-sulfamido and o-lower-alkoxy, e.g., o-methoxy, or another phenyl group ortho substituted by any other substituent of a molecular weight less than 150.

The N,N'-disubstituted amidines can readily be prepared by conventional chemical reactions, e.g., by condensation of an amino compound with triethyl orthoacetate and glacial acetic acid as taught by Taylor and Ehrhart, J. Org. Chem. 28:1108 (1963), the disclosure of which is fully incorporated by reference herein. The Taylor and Ehrhart method gives symmetrical N,N'-disubstituted acetamidines (R' =methyl). The corresponding formamidines may be prepared by substituting triethyl orthoformate in place of triethyl orthoacetate. Where R' is other than hydrogen or methyl, an appropriate substituted orthoformate may be utilized. Non-symmetrical N,N'-disubstituted amidines may be prepared by the step wise condensation of two amino compounds with triethyl orthoformate, orthoacetate or substituted orthoformate (see Examples 5, 6, 9 and 10, below). The tritiated N,N'-disubstituted amidines of the present invention may be prepared by the preparation of a halogenated precursor wherein R, R' or R'' are substituted by fluorine, chlorine, bromine or iodine, followed by treatment with tritium gas and a conventional hydrogenation catalyst such as Pt, Pd or Ni.

Included as well in the present invention are pharmaceutical compositions comprising an effective amount of the N,N'-disubstituted amidines in combination with a pharmaceutically acceptable carrier.

Compositions within the scope of this invention include all compositions wherein the N,N'-disubstituted amidine is contained in an amount which is effective to achieve its intended purpose. While individual needs vary, determination of optimal ranges of effective amounts of each component is with the skill of the art. Typically, they may be administered to mammals, e.g. humans, orally at a dose of 0.0025 to 15 mg/kg, or an equivalent amount of the pharmaceutically acceptable salt thereof, per day of the body weight of the mammal being treated for psychosis, anxiety disorders, e.g., generalized anxiety disorder, phobic disorders, obsessional compulsive disorder, panic disorder, and post traumatic stress disorders or for treatment of hypertension. Preferably, about 0.01 to about 10 mg/kg is orally administered to treat or prevent such disorders. For intramuscular injection, the dose is generally one-half of the oral dose. For example, a suitable intramuscular dose is about 0.0025 to about 15 mg/kg, and most preferably, from about 0.01 to about 10 mg/kg.

The unit oral dose may comprise from about 0.25 to about 400 mg, preferably about 0.25 to about 100 mg of the N,N'-disubstituted amidine. The unit dose may be administered one or more times daily as one or more tablets each containing from about 0.10 to about 300, conveniently about 0.25 or 50 mg of the N,N'-disubstituted amidine or its solvates.

It will be appreciated that the actual preferred amounts of active compounds used will vary according to the particular indication, specific compound being utilized, the particular compositions formulated, the mode of application, and the particular site of administration, as well as the age, general health, and concurrent treatment of the patient. Optimal administration rates for a given protocol of administration can be readily ascertained by those skilled in the art using conventional dosage determination tests conducted with regard to the foregoing guidelines.

In addition to administering the compound as a raw chemical, the anxiolytic compounds may be administered as part of a pharmaceutical preparation containing suitable pharmaceutically acceptable carriers comprising excipients and auxiliaries which facilitate processing of the anxiolytic compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethylstarch, cross-linked polyvinyl pyrrolidone, agar, or alginic acid or a salt thereof, such as sodium alginate. Auxiliaries are, above all, flow-regulating agents and lubricants, for example, silica, talc, steric acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers.

The invention is related to the discovery that certain N,N'-disubstituted amidines have a high affinity for the sigma receptor. The term "high affinity to sigma receptor" means the compound exhibits an $IC_{50}$ of less than 1000 nM, more preferrably less than 500 nM, most preferrably, less than 100 nM in a sigma receptor binding assay, preferably against $^3$H-DTG as disclosed in the examples, below. Alternatively, the compounds may be tested against $(+)$-$[^3H]$3-PPP as described by Largent, B. L. et al., *Mol. Pharmacol.* 32:772-784 (1987); Largent B. L. et al., *Eur. J. Pharmacol.* 155:345-347 (1988); and Wikstrom, H. et al., *J. Med. Chem.* 30:2169-2174 (1987). The values of $IC_{50}$ obtained by screening against $^3$H-DTG and $(+)$-$[^3H]$3-PPP are well correlated. See Weber, E. et al ., *Proc. Natl . Acad. Sci . USA* 83: 8784-8788 (1986).

The level of sigma receptor activity of the disubstituted amidines can also be determined in vivo in a discriminative stimulus property test employing rats trained to discriminate between intraperitoneal injections of cyclazocine (2.0 mg/kg) and saline in a discrete-trial avoidance paradigm with sessions of 20 trials each.

Although the discussion hereinafter of the experiments below relates to certain of these selective sigma receptor ligands, viz., the N,N'-disubstituted amidines below, the activity and utility of that compound apply comparably to the other disubstituted amidines which compete with and displace in vitro N,N'-di-(4-$[^3H]$-2-methylphenyl)-guanidine bound in vitro to isolated guinea pig brain membrane.

In carrying out the sigma receptor binding activity measurement method of this invention, a known amount of a mammalian brain membrane, e.g., human or other primate, porcine, rodent, e.g., rat or guinea pig, which has SKF-10,047 and like psychotomimetic benzomorphan binding activity is contacted in a suitable aqueous vehicle, e.g., physiological saline solution, with a mixture, usually in a solution in a suitable aqueous vehicle of (i) a tritium-labeled N,N'-disubstituted amidine having sigma receptor binding activity, in an amount capable of being fully bound to the abovesaid amount of membrane and (ii) a water soluble organic compound whose sigma receptor activity is to be assayed, in known amounts, sufficiently varied to obtain a dose-response curve. The techniques for obtaining a dose-response curve are standard and well known to those skilled in the art. Typically, one could employ molar amounts varying as much as from $10^{-3}$ to $10^3$ of the molar amount of the tritium labeled compound present in the mixture, e.g., employing from 10 to 120 and preferably 30 to 90 such mixtures.

If the organic compound being assayed has sigma receptor binding activity, a portion of the tritium labeled compound which, in the absence of the organic compound would bind to the membrane remains unbound and is thus separable from the membrane. The amount which remains unbound is proportional to the sigma receptor binding activity of the organic compound and the molar ratio thereof in the mixture to the tritium labeled compound. The two compounds can be employed at any convenient collective concentration, e.g., from $10^{-8}$ to $10^3$ mM.

In the next step, the membrane is separated from and washed until free of the solution in which step (a) is conducted. In the next step, the amount of tritium labeled compound which is thus separated from the membrane is determined, e.g., by measuring the collective radioactivity level of the separated solution and wash water and comparing that radioactivity to that obtained when the foregoing steps are conducted with the same amount of tritium-labeled N,N'-disubstituted amidine in the absence of the organic compound.

In the next step of the method, the activity of sigma receptor binding activity of the organic compound is determined from the dose response curve thus obtained.

All of the foregoing steps are conventional and have been employed in the prior art with other types of $^3$H-labeled compounds having sigma receptor binding activity. The method of this invention is, however, unique in that the tritium-labeled N,N'-disubstituted amidines of this invention are highly selective to binding by the sigma receptors and therefore will not compete with organic compounds which bind to other brain receptors.

The characterization of sigma receptors in vitro has been difficult because of the lack of selective drug ligands. Most benzomorphan opiates cross-react with other (mu, delta, kappa) opioid receptors and are therefore of only limited value for characterizing and isolating receptors. Pasternak et al., *J. Pharmacol. Exp. Ther.* 219:192-198 (1981); Zukin, R. S. et al., *Mol. Pharm.* 20:246-254 (1981); and Tam, S. W., *Eur. J. Pharmacol.* JL9:33-41 (1985). $[^3H]$DTG binds specifically and with high affinity to a single class of binding sites in guinea pig brain membranes. The binding characteristics and the drug specificity profile of these sites are concordant with those proposed for the sigma receptor, including 1) naloxone insensitivity and stereoselectivity for dextrorotatory isomers of benzomorphan opiates such as $(+)$SKF-10,047, $(+)$cyclazocine and $(+)$pentazocine; 2) high affinity for haloperidol and certain phenothiazine antipsychotic drugs; 3) stereoselectivity for $(-)$butaclamol; and 4) insensitivity to dopamine and apomorphine. $[^3H]$-DTG is one of only two known tritiated compounds that are selective for the sigma site. The other, $(+)[^3H]$3-PPP, originally proposed to be a dopamine autoreceptor agonist, has recently been shown to be selective for sigma sites in rat brain membrane binding assays. Largent et al. (1984), supra. Our experiments confirm these findings in the guinea pig and show that $[^3H]$DTG and $(+)[^3H]$3-PPP have virtually identical receptor binding characteristics and drug selectivity profiles. Previous studies have shown that sigma sites can also be labeled with (+)[³H]SKF-10,047, (+)[³H]-ethylketazocine and with (±)[³H]SKF-10,047. However, these ligands are not selective for the sigma site and require the presence of appropriate drugs in the binding assays to mask cross-reacting nonsigma binding sites.

The sigma site is clearly not related to conventional (mu, delta, kappa) opioid receptors as it is naloxone insensitive and shows stereoselectivity for dextrorotatory isomers of benzomorphan drugs. This is a reversed stereoselectivity compared to naloxone-sensitive opioid receptors which are selective for levorotatory isomers of opiates. Sigma receptors should therefore not be referred to as sigma Nopioid" receptors. The drug selectivity of sigma sites for dextrorotatory isomers of psychotomimetic opiates does, however, correlate well with the pharmacological profile of dextrorotatory versus levorotatory opiates in animal tests designed to differentiate between conventional opioid receptor activity and sigma (behavioral) activity of benzomorphan drugs. Cowan, A., *Life Sci.* 28:1559–1570 (1981); Brady, K. T. e.t. a.l., *Science* 215:178–180 (1982); and Khazan, N. et al., *Neuropharmacol.* 23:983–987 (1984).

Perhaps the most important aspect of the findings on the drug specificity of sigma sites that have emerged from this and other studies is that they interact with certain very potent antipsychotic drugs (haloperidol, phenothiazines) that are used clinically to treat schizophrenia. This intriguing drug selectivity profile facilitates studies aimed at investigating the role of sigma receptors in antipsychotic drug action and abnormal brain function. The availability of N,N'-disubstituted amidines as selective sigma ligands should serve to facilitate such studies.

The compounds of this invention have highly selective affinity for the sigma receptor. Consequently, they may have some of the activities of the benzomorphans, i.e., those produced by binding to the haloperidol-sensitive sigma receptor but not those produced by the binding of benzomorphans to other non-sigma receptors. For instance, benzomorphans may act at sigma receptors to cause mydriasis and tachycardia and pronounced psychotomimetic effects. The N,N'-disubstituted amidines are, therefore, an effective tool to demonstrate the physiological effects mediated by the sigma receptor which are often obscured by cross-reactivity of benzomorphans with non-sigma receptors. Additionally, at least some of the N,N'-disubstituted amidines are antagonists of the sigma receptors in the nerve terminals in the mouse vas deferens, where sigma receptors stimulate noradrenaline release (a phenomenon discovered by us and which provides a new screening test for CNS-stimulants and depressants), and thus are blood pressure lowering (antihypertensive) agents. Other compounds of the invention are agonists and thus increase blood pressure. Those which are antagonists to the sigma receptor binding activity, e.g., on the sigma sites of mouse vas deferens, of hallucinogenic benzomorphans, e.g., (+)3-PPP and TCP, are useful in the amelioration of the symptoms of a psychotic mental illness associated with the hallucinations, e.g., schizophrenia.

The compounds of this invention are particularly valuable in the treatment of humans afflicted with a psychotic disease, e.g., schizophrenia, or with chronic hypertension. In this regard, they can be employed in substantially the same manner as known antipsychotic agents and anti-hypertensive agents, respectively.

In carrying out the method of treatment, e.g., treating a human being suffering from a psychotic mental illness associated with hallucinations, there is administered thereto a water-soluble N,N'-disubstituted amidine which is an antagonist to the sigma receptor binding activity of a hallucinogenic benzomorphan, in an amount effective to ameliorate the hallucinations. Preferably, the amidine is a compound of Formula III wherein R and R" each is an alkyl group of 1–8 carbon atoms, a cycloalkyl group of at least 3 carbon atoms or a carbocyclic aryl group of at least 6 carbon atoms; and R' is lower alkyl, most preferably, methyl. In preferred aspect, the human being is schizophrenic; in another preferred aspect, the compound is N,N'-bis(4-bromo-2-tolyl)acetamidine, N,N'-bis(2-ethylphenyl)acetamidine, N,N'-bis(o-methylphenyl)acetamidine, N,N'-bis(adamantan-1-yl)acetamidine, N-(adamantan-1-yl)-N'-(o-methylphenyl)acetamidine, N-(o-methylphenyl)-N'-(cyclohexyl)acetamidine, N,N'-bis(3-ethylphenyl)acetamidine, N,N'-bis(2-isopropylphenyl)-acetamidine, N-exonorbornyl-N'-(2-methylphenyl)-acetamidine, N-(adamantan-1-yl)-N'-(cyclohexyl)-acetamidine, N,N'-bis(1-naphthyl)acetamidine, N-(p-tolyl)-N'-methylacetamidine, N-(1-naphthyl)-N'-(3-ethylphenyl)acetamidine, N-(1-naphthyl)-N'-( 2-isopropylphenyl)acetamidine, N-(1-naphthyl)-N'-(m-ethylphenyl)-acetamidine, N-(adamantan-2-yl)-N'-(o-methylphenyl)acetamidine, N,N'-di-(endonorbornyl)acetamidine, N,N'-di-(exonorbornyl)acetamidine, N-endonorbornyl-N'-(o-tolyl)acetamidine, N-endonorbornyl-N'-(o-iodophenyl)acetamidine, N-exonorbornyl-N'-(o-tolyl)acetamidine, N-exonorbornyl-N'-(o-iodophenyl)acetamidine, N-isobornyl-N'-(o-tolyl)acetamidine, or a corresponding compound bearing 1, 2, 3 or more additional or other substituents on one or both hydrocarbon groups, e.g., alkyl of 1–8 carbon atoms, e.g., methyl, ethyl; hydroxyalkyl of 1–8 carbon atoms; halo, e.g., chloro, bromo, iodo, fluoro; hydroxy; nitro; azido; cyano; isocyanate; amino; lower-alkylamino; di-lower-alkylamino; trifluoromethyl; alkoxy of 1–8 carbon atoms, e.g., methoxy, ethoxy and propoxy; acyloxy, e.g., alkanoyloxy of 1–8 carbon atoms, e.g., acetoxy and benzoyl; amido, e.g., acetamido, N-ethylacetamido; carbamido, e.g., carbamyl, N-methylcarbamyl, N,N'-dimethyl carbamyl; etc.

The N,N'-disubstituted amidines of the invention can act in an agonistic, antagonistic or inverse agonistic manner in relation to the prototypical sigma benzomorphans. Those which act as antagonists can therefore be expected to affect pupil size, heart rate and mentation in a direction opposite that caused by benzomorphans which can be determined by standard tests in laboratory animals. The type and level of activity for a given dosage of each compound can be, conventionally determined by routine experimentation using well known pharmacological protocols for each of the activities; the corresponding indications treatable at that dosage will be well known to skilled workers based on the pharmacological results. The compounds of this invention are particularly noteworthy for their antipsychotic activity to treat psychotic conditions, e.g., schizophrenia, by analogy to the known agents prolixin and haloperidol and for diagnosing sigma receptor intoxicated conditions.

The tritiated N,N'-disubstituted amidines of this invention are useful as a screening tool for compounds which are selective ligands for the sigma receptor binding site. As such, they are useful for screening for compounds useful for the diagnosis and treatment of sigma receptor mediated hallucinogenic mental disorders. For example, such a compound which is an agonist to a putative natural ligand will temporarily exacerbate such a mental disorder which is the result of an overabundance of the endogenous ligand and will ameliorate a mental disorder which is the result of an abnormal insufficiency of the natural ligand. The converse occurs when the disubstituted amidine is an antagonist to the putative endogenous ligand. In either case, the temporary alteration of the mental disorder by the administered ligand confirms that it is a sigma receptor associated disease, thereby eliminating other possible causes thereof, e.g., chemical toxicity, and facilitating the treatment thereof.

The N,N'-disubstituted amidines also bind to human brain membrane receptors with high affinity. Therefore another use of N,N'-disubstituted amidines is to explore the neurochemistry of mental disease by measuring the fluctuations in receptor density or function in post-mortem tissue of patients manifesting psycho- or neuropathology as contrasted with tissue from normals (unaffected controls). This topic can be studied by both receptor binding assays and autoradiography.

The invention also relates to the treatment of anxiety by administering the N,N'-disubstituted amidines of the invention. These N,N'-disubstituted amidines may exhibit anxiolytic activities at least 100-1000 times greater than that of benzodiazepines. However, unlike benzodiazepines, the substituted amidines employed in this invention are non-sedative. Therefore, these substituted amidines are particularly useful for the treatment or prevention of anxiety in animals.

The anxiolytic activity of any particular N,N'-disubstituted amidine may be determined by use of any of the recognized animal models for anxiety. A preferred model is described by Jones, B. J. et al., *Br. J. Pharmacol.* 93:985-993 (1988). This model involves administering the compound in question to mice which have a high basal level of anxiety. The test is based on the finding that such mice find it adversive when taken from a dark home environment in a dark testing room and placed in an area which is painted white and brightly lit. The test box has two compartments, one white and brightly illuminated and one black and non-illuminated. The mouse has access to both compartments via an opening at floor level in the divider between the two compartments. The mice are placed in the center of the brightly illuminated area. After locating the opening to the dark area, the mice are free to pass back and forth between the two compartments. Control mice tend to spend a larger proportion of time in the dark compartment. When given an anxiolytic agent, the mice spend more time exploring the more novel brightly lit compartment and exhibit a delayed latency to move to the dark compartment. Moreover, the mice treated with the anxiolytic agent exhibit more behavior in the white compartment, as measured by exploratory rearings and line crossings. Since the mice can habituate to the test situation, naive mice should always be used in the test. Five parameters may be measured: the latency to entry into the dark compartment, the time spent in each area, the number of transitions between compartments, the number of lines crossed in each compartment, and the number of rears in each compartment. It is expected that the administration of an N,N'-disubstituted amidine will result in the mice spending more time in the larger, brightly lit area of the test chamber. Unlike diazepam, the N,N'-disubstituted amidines are not expected to cause significant decreases in the numbers of line crossings and rears. Thus, these N,N'-disubstituted amidines are expected to exhibit potent anxiolytic activity, and at the same time, are expected to be nonsedating.

In the light/dark exploration model, the anxiolytic activity of a putative agent can be identified by the increase of the numbers of line crossings and rears in the light compartment at the expense of the numbers of line crossings and rears in the dark compartment, in comparison with control mice.

A second preferred animal model is the rat social interaction test described by Jones, B. J. et al., supra, wherein the time that two mice spend in social interaction is quantified. The activity of a putative anxiolytic agent can be identified by the increase in the time that pairs of male rats spend in active social interaction (90% of the behaviors are investigatory in nature). Both the familiarity and the light level of the test arena may be manipulated. Undrugged rats show the highest level of social interaction when the test arena is familiar and is lit by low light. Social interaction declines if the arena is unfamiliar to the rats or is lit by bright light. Anxiolytic agents prevent this decline. The overall level of motor activity may also be measured to allow detection of drug effects specific to social behaviors.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. The entire text of all applications, patents and publications, if any, cited above and below are hereby incorporated by reference.

EXAMPLES

In the foregoing and in the following examples, all temperatures are set forth uncorrected in degrees Celsius and unless otherwise indicated, all parts and percentages are by weight.

EXPERIMENTAL

In the following examples, melting points were determined in open capillary tubes on a Thomas-Hoover apparatus (compounds melting 230° C.) or on a Melt-Temp (compounds melting > 230° C.) and are uncorrected. The NMR spectra of all compounds were recorded on a General Electric QE-300, and chemical shifts are reported in ppm relative to the residual signal of the deuterated solvent (CHCl$_3$, 7.26 ppm; HCD$_2$OD, 3.30 ppm). IR spectra were recorded on a Nicolet 5DXB FT-IR, or a Perkin-Elmer model 1420 in CHCl$_3$ or neat. IR and NMR spectra of all compounds are consistent with their assigned structures. Elemental analyses were performed by Desert Analytics (Tuscon, Ariz.) or Galbraith Laboratories (Knoxville, Ten.).

EXAMPLE 1

N,N'-Bis(4-bromo-2-tolyl)acetamidine

Following the procedure of Taylor and Ehrhart (Taylor, E. C. et al., *J. Org. Chem.* 28:1108 (1963)), a stirred solution, under N$_2$, of 4-bromo-2-methylaniline (5.01 g, 2.69 mmol), triethyl orthoacetate (2.38 g, 14.7 mmol) and glacial acetic acid (1.11 g, 18.5 mmol) was heated at reflux (95° C.) in an oil bath. After 2.5 hours at reflux the temperature of the oil bath was raised to 130° C. and volatile materials were distilled off through a short distillation head. During the distillation a white solid formed in a reaction flask. This white solid material was collected then crystallized from boiling ethanol (300 ml) to give 2.42 g of white crystals, Mp 198.5-201.5 C. Recrystallization of 958 mg from 100 ml of boiling ethanol gave 642 mg of white crystals as small plates, Mp 199°-200.5° C.:

$^1$H NMR (CD$_3$OD) δ 1.86 (s, 3 H), 2.20 (s, 6 H), 6.99 (bs, 2 H), 7.26 (d, 2H, J=8.3 Hz), 7.35 (s, 2 H).

Anal. Calcd. for C$_{16}$H$_{16}$N$_2$Br$_2$: C, 48.51; H, 4.07; N, 7.07. Found: C, 48.36; H, 4.10; N, 6.99

EXAMPLE 2

N,N'-Bis(2-ethylphenyl)acetamidine

Following the procedure for Taylor and Ehrhart ((Taylor, E. C. et al., *J. Org. Chem.* 28:1108 (1963)), a stirred solution, under N$_b$ 2, of 2-ethylaniline (2.14 g, 17.7 mmol), triethyl orthoacetate (1.37 g, 8.5 mmol) and glacial acetic acid (0.45 ml, 7.9 mmol) was refluxed at 95°-110° for 2.5 hours. The resulting clear light brown solution was heated (oil bath temperature was 195° C.) under vacuum (30 Mm Hg) and the volatile materials were recovered through a short distillation head. The brown oil residue was dissolved in 10 ml of diethyl ether then extracted with 10 ml of 0.6N sodium carbonate. The layers were separated and the aqueous layer was extracted with 2×10 ml of diethyl ether. The combined organic layers were dried (Na$_2$SO$_4$) and the solvent removed at reduced pressure to give 1.15 g of light brown solid. Distillation (bulb to bulb, 190°-200°/0.5 Mm) gave 1.13 g of light brown oil that solidified on standing. Crystallization from 20 ml of boiling petroleum ether gave 595 mg of white crystals, Mp 80°-82° C. Recrystallization of 421 mg from 2 ml of boiling petroleum ether gave 380 mg of white granular crystals Mp 80°-81.5° C.

$^1$H NMR (CD$_3$OD) δ 1.91 (t, 6 H, J=7.5 Hz), 1.87 (s, 3 H), 2.62 (q, 4 H, J=7.5 Hz), 6.78-7.85 (m, 8H).

Anal. Calcd. for C$_{18}$H$_{22}$N$_2$: C, 81.16; H, 8.32; N, 10.52. Found: C, 81.42; H, 8.33; N, 10.49.

EXAMPLE 3

N,N'-Bis(o-methylphenyl)acetamidine

According to literature ((Taylor, E. C. et al., *J. Org. Chem.* 28:1108 (1963)), a solution of o-toluidine (4.28 g, 40.0 mmol) and triethyl orthoacetate (3.24 g, 290 mmol) in acetic acid (I ml) was heated to reflux for 2 h. Volatile compounds were distilled off (120°-140°, 20 mm) and the solid residue was extracted with ether (total of 50 ml) in presence of 1N solution of Na$_2$CO$_3$ in water (100 ml). Two fold recrystallization from hexane-5% toluene gave white but still impure amidine (1.85 g, 38%); Mp 65°-68° (Lit (Taylor et al., supra) 70°, Lit (Barluenga, J. et al., *Perkin* 1 2732 (1980) 134°-135°). On chromatography with hexanes-ether 2:1 some unreacted o-toluidine was removed as the least polar fraction (TLC ether 0.75). Intermediate fractions contained colorless N-tolyl acetimidate. Almost pure amidine (TLC ether 0.46) was eluted with hexanes-ether 1:1. This compound was further purified by chromatography with THF-hexanes 1:1 then 1:0 and filtration of the eluents through celite for the removal of turbid matter. The addition of HCl gas saturated ether (5 ml) to a solution of the amidine (313 mg, 1.31 mmol) in ether (10 ml) gave the new hygroscopic, hydrochloride of the title compound (318 mg, 88%), Mp 237°-239°.

$^1$H NMR δ 1.91 (s, 3 H. CH$_3$-tolyl), 7.16-7.35 (m, 8 H, H-aromat), 10.5 (broad s, 2 H NH$_2$).

MS (Barker, J. et al., *Org. Mass. Spectrum* 20:619 (1985)) 238 (M+, 24), 223 (10) 132 (100), 91 (56), 65 (30). Anal. Calcd. for C$_{16}$H$_{19}$N$_2$Cl: C, 69.93; H, 6.97; N, 10.19. Found: C, 69.82; H, 6.87; N, 10.09.

EXAMPLE 4

N,N'-Bis(adamantan-1-yl)acetamidine

A mixture of adamantyl amine (12.08 g, 40 mmol) and glacial acetic acid (2.4 g, 20 mmol) was placed in preheated oil bath (150° C.) and then the temperature was raised to 215° C. and after 15 min the resulting semisolid was allowed to cool back to 160° C. Now triethyl orthoacetate (6.48 g, 20 mmol) was added cautiously drop after drop. The reaction became exothermic and during this time the reflux condenser was replaced by a distillation condenser and the low volatiles were distilled off at 75°-80° C. (head temperature). Dichloromethane (50 ml) was added to the resulting brown solid and then washed with dil. sodium bicarbonate. The organic layer was dried over sodium sulfate, filtered and concentrated to give an off-white solid. It was flash chromatographed on silica gel using CH$_2$Cl$_2$ (100%) followed by CH$_2$Cl$_2$:MeOH (9:1) as eluents to give the title compound (0.859 g, 3.5%) as bright white solid. Mp 255°-58° C.

IR (CHCl$_3$): 1630 cm$^{-1}$.

$^1$H NMR (CDCl$_3$): δ 9.94 (s, 1H), 2.37-1.63 (m, 30 H), 1.66 (s, 3 H).

EXAMPLE 5

N-(Adamantan-1-yl)-N'-(o-methylphenyl)acetamidine

Glacial acetic acid (catalytic amount, 4 drops) was added to a mixture of o-toluidine (1.07 g, 10 mmol) and triethyl orthoacetate (1.94 g, 12 mmol) and the resulting clear solution was heated to reflux on oil bath (140° C.) under nitrogen. After 90 min the reflux condenser was replaced by distillation condenser and the low volatiles were distilled off at 75°-80° C. heat temperature. The undistilled brown liquid was cooled to room temperature and then dried on manifold at 0.5 mm Hg for about 30 min. Now adamantyl amine (1.36 g, 10 mmol) was added to this and the resulting suspension was heated on oil bath at 155° C. for 5 min to give a clear brown solution. Catalytic amount (5 drops) of glacial acetic acid was added and the heating continued at 185° C. for 12 hours. It was allowed to cool to room temperature and dichloromethane (50 ml) was added and the undissolved solid was discarded. The organic phase was concentrated and then purified by flash chromatography over silica gel using CH$_2$Cl$_2$ followed by CH$_2$Cl$_2$:CH$_3$CN (7:3) as eluents to give the product as a thick brown liquid. It was then treated with excess of ether-HCl solution and the resulting white powder was filtered and dried to give the hydrochloride salt of the title compound (0. 246 g, 8.6%) as bright white needles. Mp 280°-81° C.

IR (CHC13): 1630 cm$^{-1}$.

$^1$H NMR (CDCl$_3$): δ 7.29-7.03 (m, 4 H), 2.33-1.72 (m, 15 H), 2.14 (s, 3 H), 1.58 (s, 3 H).

Anal. Calcd. for C$_{18}$H$_{27}$N$_2$Cl: 71.54; H, 8.53; N, 8.79. Found: C, 71.54; H, 8.45; N, 8.79.

EXAMPLE 6

N-(o-Methylphenyl)-N'-(cyclohexyl)acetamidine

Glacial acetic acid (catalytic amount, 5 drops) was added to a mixture of o-toluidine (1.07 g, 10 mmol) and triethyl orthoacetate (1.94 g, 12 mmol) and was heated at 120° C. for 60 min. The reflux condenser was replaced by a distillation condenser and the low volatiles were distilled off at 74°-76° C. (head temperature). The undistilled residue was dried under manifold vacuum to give a light yellow liquid. Now cyclohexyl amine (0.99 g, 10 mmol) followed by catalytic amount (0.1 ml) of glacial acetic acid was added and the resulting suspension was heated on oil bath at 140° C. for 12 hr. The reflux condenser was replaced by a distillation condenser and the low volatiles including unreacted cyclohexyl amine were removed under manifold vacuum (0.5 mm Hg). After it cooled to room temperature, dichloromethane (30 ml) was added and then it was washed with dil. sodium bicarbonate solution. The organic phase was dried over $Na_2SO_4$, filtered and concentrated to give an off-white solid. It was crystallized twice from 95 EtOH-H20 to give the title compound (0.636 g, 24%) as bright white needles. Mp 130°-31° C.

IR ($CHCl_3$): 3450, 1640 cm$^{-1}$.

$^1$H NMR ($CDCl_3$): δ 7.13 (m, 4 H), 2.10 (s, 3 H), 1.75-1.10 (m, 11 H), 1.65 (s, 3 H).

Anal. Calcd. for $C_{14}H_{22}N_3Cl$: C, 62.77; H, 8.28; N, 15.69. Found: C, 62.61; H, 8.37; N, 15.61.

EXAMPLE 7

N,N'-Bis(3-ethylphenyl)acetamidine

A mixture of 3-ethylaniline (1.0 g, 8.25 mmol), triethyl orthoacetate (0.670 g, 4.13 mmol) and glacial acetic acid (0.019 ml, 0.33 mmol) was heated to reflux in an oil bath at 125-140° C. for 3 hr. It was purified by flash chromatography on silica gel and the product was then crystallized from pet-ether-dichloromethane to give the title compound (0.770 g, 72%) as an off-white soft crystal. Mp 86°-87° C.

IR ($CHCl_3$): 3440, 3380 and 1650 cm$^{-1}$.

EXAMPLE 8

N,N'-Bis(2-isopropylphenyl)acetamidine

A mixture of 2-isopropylaniline (1.0 g, 7.4 mmol), triethyl orthoacetate (0.68 ml, 3.7 mmol) and glacial acetic acid (0.1 ml, 1.75 mmol) was heated at 140° C. on an oil bath for 5 hr. It was allowed to cool to room temperature then dissolved in dichloromethane and washed with dil. sodium bicarbonate solution. The organic phase was dried over $Na_2SO_4$, filtered and concentrated on rotavapor under reduced pressure. The residue was crystallized from pet-ether (storing in refrigerator for overnight) to afford the title compound (0.496 mg, 46%) as clear crystals.

MP: 94°-96° C.

IR ($CHCl_3$): 3380, 1640 cm$^{-1}$.

EXAMPLE 9

N-Exonorbornyl-N'-(2-methylphenyl)acetamidine

A mixture of 2-methylaniline (1.07 g, 10 mmol), triethyl orthoacetate (1.94 9, 12 mmol) and glacial acetic acid (catalytic amounts, drops) were heated on oil bath at 125° C. for 1.5 hr. The reflux condenser was replaced by distillation condenser and the low volatiles were distilled off at 74°-76° C. (head temperature). The residue further was dried on manifold for 3 hr to give the intermediate imidate as a colorless thick liquid. An aliquot of this imidate (0.826 g, 5 mmol), exo-norbornyl amine (0.556 g, 5 mmol) and catalytic amount of glacial acetic acid (5 drops) were heated on oil bath at 125° C. for 15 hr. It was allowed to cool to room temperature and dried on manifold for about 1 hour to remove the low volatiles and then it was triturated with pet-ether to give a white solid. It was crystallized from 95% EtOH-$H_2O$ to give the title compound (0.286 g, 23.6%) as white needles. Mp: 149°-51° C.

IR ($CHCl_3$): 3440, 1640 cm$^{-1}$.

$^1$N NMR ($CDCl_3$): δ 7.17-6.62 (m, 4 H), 2.35-1.06 (m, 11 H), 2.10 (s, 3 H), 1.64 (s, 3 H).

EXAMPLE 10

N-(Adamantan-1-yl)-N'-(cyclohexyl)acetamidine

Adamantyl amine (1.87 g, 10 mmol), triethyl orthoacetate (1.62 g, 10 mmol) and cyclohexyl amine (0.99 g, 10 mmol) were mixed together then placed in preheated oil bath (140° C.) under nitrogen. After 5 min the reaction became exothermic and the reaction mixture became a slurry and upon continuation for 20 min it became a clear colorless solution. Now the reflux condenser was then replaced by distillation condenser and the low volatiles were distilled off at 75°-77° C. (head temperature) and later the undistilled residue was dried on manifold to give a light-yellow solid. The crude product was flash chromatographed on silica gel using chloroform as eluent to afford the title compound (0.076 g, 2.78%) as a white solid.

Mp: 185°-87° C.

IR ($CHCl_3$): 1650 cm$^{-1}$.

EXAMPLE 11

Sigma Receptor Binding Assays

Sigma receptor binding assays using guinea pig brain membrane homogenates and the radioligands [$^3$H]DTG and (+)[$^3$H]3-PPP are done as previously described (Weber et al., *P.N.A.S. (USA)* 83:8784-8788 (1986)). Briefly, frozen whole guinea-pig brains (Biotrol, Indianapolis, Ind.) are homogenized in 10 volumes (w/v) of ice-cold 320 mM sucrose using a Brinkman polytron. The homogenate is centrifuged at 1,000×g for 20 minutes at 4° C. The supernatant is centrifuged at 20,000×g for 20 minutes at 4° C. The resulting pellet is resuspended in 10 initial volumes of 50 mM Tris/HCl buffer at pH 7.4 and centrifuged at 20,000×g for 20 minutes at 4° C. The resulting pellet is resuspended in 5 initial volumes ice-cold 50 mM Tris/HCl (pH 7.4), and the final volume is adjusted to yield a protein concentration of 3 mg/ml, as determined by dye-binding protein assay (Biorad) using BSA as the standard. Aliquots of 20-ml are stored at 770° C. until used, with no detectable loss of binding.

For [$^3$H]DTG binding assays, 20-ml aliquots of the frozen membrane suspension are thawed and diluted 1:3 in 50 mM Tris/HCl (pH 7.4). To 12×75 mm polystyrene test tubes are added 0.8 ml of diluted membrane suspension, 0.1 ml of [$^3$H]DTG (46 Ci/mmol; see Weber et al., *P.N.A.S (USA)* 83 :8784-8788 (1986)) or (+)[$^3$H]3-PPP (NEN, 98 Ci/mmol) to yield a final concentration of 1.4 nM, and 0.1 ml of unlabelled drugs or buffer. The protein concentration in the 1-ml final incubation volume is 800 ug/ml, corresponding to 32 mg of brain tissue (original wet weight) and to a tissue concentration within the linear range for specific binding. Non-specific binding is defined as that remaining in the presence of 10 uM haloperidol. Specific binding constituted 90% of total [³H]DTG binding. Incubations are terminated after 90 minutes at room temperature by addition of 4 ml of ice-cold 50 mM Tris/HCl (pH 7.4) and rapid filtration of the membrane suspension through Whatman GF/B glass-fiber filters under vacuum, using a 48-well cell harvester (Brandel, Baithersburg, Md.). The filters are washed 2 times with 4 ml of 50 mM Tris/HCl (pH 7.4). Total filtration and washing time is less than 20 seconds. Each filter is suspended in 10 ml Cytoscint (Westchem, San Diego, Calif.), and radioactivity is measured by liquid scintillation spectrometry at a counting efficiency of approximately 50%. IC$_{50}$ values are determined by interpolation from displacement-curve plots on semilogarithmic graph paper.

The IC$_{50}$ binding values (nM) are listed in Table I:

| SIGMA RECEPTOR BINDING AFFINITY OF N,N'-DISUBSTITUTED AMIDINES | | | |
|---|---|---|---|
| | IC$_{50}$ vs [³H]DTG (nM) | | |
| Compound | MEAN | SEM | n |
| N,N'-bis(-o-tolyl)acetamidine | 15.00 | 1.31 | 4 |
| N,N'-bis(1-naphthyl)acetamidine | 169.25 | 32.25 | 4 |
| N,N'-bis(4-bromo-2-methylphenyl)-acetamidine | 25.83 | 2.84 | 4 |
| N,N'-bis-(o-ethylphenyl)acetamidine | 36.88 | 9.02 | 4 |
| N-(o-tolyl)-N'-methylacetamidine | 354.00 | 36.00 | 2 |
| N,N'-bis(adamantan-1-yl)acetamidine | 15.68 | 2.21 | 6 |
| N-(adamantan-1-yl)-N'-(2-methylphenyl)-acetamidine | 7.27 | 2.00 | 4 |
| N-(cyclohexyl)-N'-(2-methyl-phenyl)acetamidine | 9.01 | 3.11 | 4 |
| N,N'-bis(3-ethylphenyl)acetamidine | 13.00 | 2.64 | 4 |
| N,N'-bis(2-isopropylphenyl)acetamidine | 77.43 | 14.23 | 4 |
| N-(1-naphthyl)-N'-(3-ethylphenyl)-acetamidine | 123.0 | 27.0 | 4 |
| N-(1-naphthyl)-N'-(2-isopropylphenyl)-acetamidine | 117.53 | 36.96 | 4 |
| N-(1-naphthyl)-N'-(m-ethylphenyl)-acetamidine | 2412.00 | 208.45 | 3 |
| N-(exonorborn-2-yl)-N'-(o-tolyl)-acetamidine | 9.32 | 0.17 | 3 |
| N-(adamantan-1-yl)-N'-(cyclohexyl)-acetamidine | 71.90 | 12.43 | 4 |

As noted above, the compounds of this invention are useful as anti-hypertensive agents and can be used in the same manner as known antihypertensive agents, e.g., methyldopa, metoprolol tartrate and hydralazine hydrochloride.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for the treatment or prophylaxis of anxiety in an animal susceptible to anxiety comprising the administration to an animal exhibiting symptoms of anxiety or susceptible to anxiety, of an anxiolytic amount of an N,N'-disubstituted amidine having the formula:

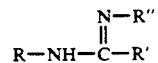

where R and R" are a cycloalkyl group of at least 5 carbon atoms, a carbocyclic aryl group of at least 6 carbon atoms, alkaryl or aralkyl of at least 6 carbon atoms and containing 1-3 separate or fused rings, or a heterocyclic ring, wherein each of R and R" may be substituted in 1-3 positions, or wherein R and R" together with the amidine group form a saturated or unsaturated cyclic ring containing at least 2 carbon atoms exclusive of the amidine carbon atom, wherein said cyclic ring may be substituted with one or more alkyl groups of 1-6 carbon atoms, carbocyclic aryl groups of at least 6 carbon atoms, cycloalkyl groups of 3-12 carbon atoms, or 1-2 fused aromatic rings; and R' is hydrogen, $C_1$-$C_6$ alkyl, $C_2$-$C_6$ alkenyl, trifluoromethyl, or $C_1$-$C_6$ alkylsulfonyl.

2. The method of claim 1, wherein said N,N'-disubstituted amidine is selected from the group consisting of N,N'-bis(4-bromo-2-tolyl)acetamidine, N,N'-bis(2-ethylphenyl)acetamidine, N,N'-bis(o-methylphenyl)acetamidine, N,N'-bis(1-adamantyl)acetamidine, N-(1-adamantyl)-N'-(o-methylphenyl)acetamidine, N-(o-methylphenyl)-N'-(cyclohexyl)acetamidine, N,N'-bis(3-ethylphenyl)acetamidine, N,N'-bis(2-isopropylphenyl)acetamidine, N-exonorbornyl-N'-(2-methylphenyl)acetamidine, N-(1-adamantyl)-N'-(cyclohexyl)acetamidine, N,N'-bis(1-naphthyl)acetamidine, N-(1-naphthyl)-N'-(3-ethylphenyl)acetamidine, N-(1-naphthyl)-N'-(2-isopropylphenyl)acetamidine, N-(1-naphthyl)-N'-(m-ethylphenyl)acetamidine, N-(2-adamantyl)-N'-(o-methylphenyl)acetamidine, N,N'-di-(endonorbornyl)acetamidine, N,N'-di-(exonorbornyl)acetamidine, N-endonorbornyl-N'-(o-tolyl)acetamidine, N-endonorbornyl-N'-(o-iodophenyl)acetamidine, N-exonorbornyl-N'-(o-tolyl)acetamidine, N-exonorbornyl-N'-(o-iodophenyl)acetamidine, and N-isobornyl-N'-(o-tolyl)acetamidine.

3. The method of claim 1 wherein R and R" may be substituted in 1-3 positions by alkyl having 1-8 carbon atoms, hydroxyalkyl having 1-8 carbon atoms, halo, hydroxy, nitro, azido, cyano, isothiocyanato, amino, lower-alkylamino, di-lower-alkylamino, trifluoromethyl, alkoxy having 1-8 carbon atoms, acyloxy, amido and carbamido.

4. The method of claim 1 wherein R and R" are each independently adamantyl, cyclohexyl, carbocyclic aryl of at least 6 carbon atoms, norbornyl or isobornyl.

5. The method of claim 1 wherein R and R" are each independently adamantyl, cyclohexyl, a carbocyclic aryl group of at least 6 carbon atoms, norbornyl or isobornyl, and R' is $C_1$-$C_6$ alkyl.

6. The method of claim 1 wherein R and R" are each independently adamantyl, phenyl or norbornyl.

7. The method of claim 1 wherein R and R" are each independently adamantyl or phenyl.

8. The method of claim 5 wherein R' is $C_1$-$C_6$ alkyl.

9. The method of claim 7 wherein R' is $C_1$-$C_6$ alkyl.

10. The method of claim 5 wherein R' is methyl.

11. The method of claim 7 wherein R' is methyl.

12. The method of claim 1 wherein R is adamantyl, R' is $C_1$-$C_6$ alkyl, and R" is phenyl.

13. The method of claim 12 wherein R' is methyl.

14. The method of claim 1 wherein R and R" are each phenyl and R' is $C_1$-$C_6$ alkyl.

15. The method of claim 14 wherein R' is methyl.

16. A method for the treatment or prophylaxis of anxiety in an animal susceptible to anxiety comprising the administration to an animal exhibiting symptoms of anxiety or susceptible to anxiety comprising the administration to an animal exhibiting symptoms of anxiety or susceptible to anxiety, of an anxiolytic amount of an N,N'-disubstituted amidine having the formula:

wherein
- X and Y are independently a branched or straight chain $C_1$-$C_8$ unsaturated alkylene;
- R and R" are independently a cycloalkyl group of at least 5 carbon atoms, a carbocyclic aryl group of at least 6 carbon atoms, aralkyl of at least 6 carbon atoms and containing 1-3 separate or fused rings, or a heterocyclic ring, wherein each of R and R" may be substituted in 1-3 positions, or where R and R" form a bond to give a saturated or unsaturated cyclic ring containing at least 2 carbon atoms exclusive of the amidine carbon atom, wherein said cyclic ring may be substituted with one or more alkyl groups of 1-6 carbon atoms, carbocyclic aryl groups of at least 6 carbon atoms, cycloalkyl groups of 3-12 carbon atoms, or 1-2 fused aromatic rings; and
- R' is hydrogen, $C_1$-$C_6$ alkyl, $C_2$-$C_6$ alkenyl, trifluoromethyl, or $C_1$-$C_6$ alkylsulfonyl.

17. The method of claim 16 wherein R and R" may be substituted in 1-3 positions by alkyl having 1-8 carbon atoms, hydroxyalkyl having 1-8 carbon atoms, halo, hydroxy, nitro, azido, cyano, isothiocyanato, amino, lower-alkylamino, di-lower-alkylamino, trifluoromethyl, alkoxy having 1-8 carbon atoms, acyloxy, amido and carbamido.

18. A method of treating abnormal psychotic behavior in a human being which comprises administering thereto, in an amount effective to ameliorate the abnormal psychotic behavior an N,N'-disubstituted amidine having the formula:

wherein R and R" are a cycloalkyl group of at least 5 carbon atoms, a carbocyclic aryl group of at least 6 carbon atoms, alkaryl or aralkyl of at least 6 carbon atoms and containing 1-3 separate or fused rings, or a heterocyclic ring, wherein R and R" may be substituted in -3 positions, or wherein each of R and R" together with the amidine group form a saturated or unsaturated cyclic ring containing at least 2 carbon atoms exclusive of the amidine carbon atom, and wherein said cyclic ring may be substituted with one or more alkyl groups of 1-6 carbon atoms, carbocyclic aryl groups of at least 6 carbon atoms, cycloalkyl groups of 3-12 carbon atoms, or 1-2 fused aromatic rings; and
- R' is hydrogen, $C_1$-$C_6$ alkyl, $C_2$-$C_6$ alkenyl, trifluoromethyl, or $C_1$-$C_6$ alkylsulfonyl.

19. The method of claim 18, wherein said N,N'-disubstituted amidine is selected from the group consisting of N,N'-bis(4-bromo-2-tolyl)acetamidine, N,N'-bis(2-ethylphenyl)acetamidine, N,N'-bis(o-methylphenyl)acetamidine, N,N'-bis(1-adamantyl)acetamidine, N-(1-adamantyl)-N'-(o-methylphenyl)acetamidine, N-(o-methylphenyl)-N'-(cyclohexyl)acetamidine, N,N'-bis(3-ethylphenyl)acetamidine, N,N'-bis(2-isopropylphenyl)acetamidine, N-exonorbornyl-N'-(2-methylphenyl)acetamidine, N-(1-adamantyl)-N'-(cyclohexyl)acetamidine, N,N'-bis(1-naphthyl)acetamidine, N-(1-naphthyl)-M'-(3-ethylphenyl)acetamidine, N-(1-naphthyl)-N'-(2-isopropylphenyl)acetamidine, N-(2-adamantyl)-N'-(o-methylphenyl)acetamidine, N,N'-di(endonorbornyl)acetamidine, N,N'-di-(exonorbornyl)acetamidine-N'-(o-iodophenyl)acetamidine, N-exonorbornyl-N'-(o-tolyl)acetamidine, N-exonorbornyl-N'-(o-iodophenyl)acetamidine, and N-isobornyl-N'-(o-tolyl)acetamidine.

20. The method of claim 18 wherein R and R" may be substituted in 1-3 positions by alkyl having 1-8 carbon atoms, hydroxyalkyl having 1-8 carbon atoms, halo, hydroxy, nitro, azido, cyano, isothiocyanato, amino, lower-alkylamino, di-lower-alkylamino, trifluoromethyl, alkoxy having 1-8 carbon atoms, acyloxy, amido and carbamido.

21. The method of claim 18 wherein R and R" are each independently adamantyl, cyclohexyl, carbocyclic aryl of at least 6 carbon atoms, norbornyl or isobornyl.

22. The method of claim 18 wherein R and R" are each independently adamantyl, cyclohexyl, a carbocyclic aryl group of at least 6 carbon atoms, norbornyl or isobornyl, and R' is $C_1$-$C_6$ alkyl.

23. The method of claim 18 wherein R and R" are each independently adamantyl, phenyl or norbornyl.

24. The method of claim 18 wherein R and R" are each independently adamantyl or phenyl.

25. The method of claim 23 wherein R' is $C_1$-$C_6$ alkyl.

26. The method of claim 24 wherein R' is $C_1$-$C_6$ alkyl.

27. The method of claim 23 wherein R' is methyl.

28. The method of claim 24 wherein R $\propto$ is methyl.

29. The method of claim 18 wherein R is adamantyl, R' is $C_1$-$C_6$ alkyl, and R" is phenyl.

30. The method of claim 29 wherein R' is methyl.

31. The method of claim 18 wherein R and R" are each phenyl and R' is C-$C_6$ alkyl.

32. The method of claim 31 wherein R' is methyl.

33. A method of treating abnormal psychotic behavior in a human being which comprises administering thereto, in an amount effective to ameliorate the abnormal psychotic behavior an N,N'-disubstituted amidine having the formula:

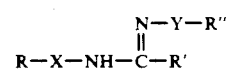

wherein
- X and Y are independently a branched or straight chain $C_1$-$C_8$ alkylene or a branched or straight chain $C_2$-$C_8$ unsaturated alkylene;
- R and R" are independently a cycloalkyl group of at least 5 carbon atoms, a carbocyclic aryl group of at least 6 carbon atoms, aralkyl of at least 6 carbon atoms and containing 1-3 separate or fused rings, or a heterocyclic ring, wherein each of R and R" may be substituted in 1-3 positions, or wherein R and R" may form a bond to give a saturated or unsaturated cyclic ring containing at least 2 carbon atoms exclusive of the amidine carbon atoms, wherein said cyclic ring may be substituted with one or more alkyl groups of -6 carbon atoms, carbocyclic aryl groups of at least 6 carbon atoms, cycloalkyl groups of 3–12 carbon atoms, or 1–2 fused aromatic rings; and R' is hydrogen, $C_1$–$C_6$ alkyl, $C_2$–$C_6$ alkenyl, trifluoromethyl, or $C_1$–$C_6$ alkylsulfonyl.

34. The method of claim 33 wherein R and R" may be substituted in 1–3 positions by alkyl having 1–8 carbon atoms, hydroxyalkyl having 1–8 carbon atoms, halo, hydroxy, nitro, azido, cyano, isothiocyanato, amino, lower-alkylamino, di-lower-alkylamino, trifluoromethyl, alkoxy having 1–8 carbon atoms, acyloxy, amido and carbamido.

35. A method of treating hypertension which comprises administering to a hypertensive person, in an amount effective to ameliorate the hypertensive state an N,N'-disubstituted amidine having the formula:

wherein R and R" are a cycloalkyl group of at least 5 carbon atoms, a carbocyclic aryl group of at least 6 carbon atoms, alkaryl or aralkyl of at least 6 carbon atoms and containing 1–3 separate or fused rings, or a heterocyclic ring, wherein each of R and R" may be substituted in 1–3 positions, or wherein R and R" together with the amidine group may form a saturated or unsaturated cyclic ring containing at least 2 carbon atoms exclusive of the amidine carbon atom, wherein said cyclic ring may be substituted with one or more alkyl groups of 1–6 carbon atoms, carbocyclic aryl groups of at least 6 carbon atoms, cycloalkyl groups of 3–12 carbon atoms, or 1–2 fused aromatic rings; and R' is hydrogen, $C_1$–$C_6$ alkyl, $C_2$–$C_6$ alkenyl, trifluoromethyl, or $C_1$–$C_6$ alkylsulfonyl.

36. The method of claim 35, wherein said N,N'-disubstituted amidine is selected from the group consisting of N,N'-bis(4-bromo-2-tolyl)acetamidine, N,N'-bis(2-ethylphenyl)acetamidine, N,N'-bis(o-methylphenyl)acetamidine, N,N'-bis(1-adamantyl)acetamidine, N-(1-adamantyl)-N'-(o-methylphenyl)acetamidine, N-(o-methylphenyl)-N'-(cyclohexyl)acetamidine, N,N'-bis(3-ethylphenyl)acetamidine, N,N'-bis(2-isopropylphenyl)acetamidine, N-exonorbornyl-N'-(2-methylphenyl)acetamidine, N-(1-adamantyl)-N'-(cyclohexyl)acetamidine, N,N'-bis(1-naphthyl)acetamidine, N-(1-naphthyl)-N'-(3-ethylphenyl)acetamidine, N-(1-naphthyl)-N'-(2-isopropylphenyl)acetamidine, N-(1-naphthyl)-N'-(m-ethylphenyl)acetamidine, N-(2-adamantyl)-N'-(o-methylphenyl)acetamidine, N,N'-di-(endonorbornyl)acetamidine, N,N'-di-(exonorbornyl)acetamidine, N-endonorbornyl-N'-(o-tolyl)acetamidine, N-endonorbornyl-N'-(o-iodophenyl)acetamidine, N-exonorbornyl-N'-(o-tolyl)acetamidine, N-exonorbornyl-N'-(o-iodophenyl)acetamidine, and N-isobornyl-N'-(o-tolyl)acetamidine.

37. The method of claim 35 wherein R and R" may be substituted in 1–3 positions by alkyl having 1–8 carbon atoms, hydroxyalkyl having 1–8 carbon atoms, halo, hydroxy, nitro, azido, cyano, isothiocyanato, amino, lower-alkylamino, di-lower-alkylamino, trifluoromethyl, alkoxy having 1–8 carbon atoms, acyloxy, amido and carbamido.

38. The method of claim 35 wherein R and R" are each independently adamantyl, cyclohexyl, carbocyclic aryl of at least 6 carbon atoms, norbornyl or isobornyl.

39. The method of claim 35 wherein R and R" are each independently adamantyl, cyclohexyl, a carbocyclic aryl group of at least 6 carbon atoms, norbornyl or isobornyl, and R' is $C_1$–$C_6$ alkyl.

40. The method of claim 35 wherein R and R" are each independently adamantyl, phenyl or norbornyl.

41. The method of claim 35 wherein R and R" are each independently adamantyl or phenyl.

42. The method of claim 40 wherein R' is $C_1$–$C_6$ alkyl.

43. The method of claim 41 wherein R' is $C_1$–$C_6$ alkyl.

44. The method of claim 40 wherein R' is methyl.

45. The method of claim 41 wherein R' is methyl.

46. The method of claim 35 wherein R is adamantyl, R' is $C_1$–$C_6$ alkyl, and R" is phenyl.

47. The method of claim 46 wherein R' is methyl.

48. The method of claim 35 wherein R and R" are each phenyl and R' is $C_1$–$C_6$ alkyl.

49. The method of claim 48 wherein R' is methyl.

50. A method of treating hypertension which comprises administering to a hypertensive person, in an amount effective to ameliorate the hypertensive state an N,N'-disubstituted amidine having the formula:

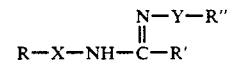

wherein

X and Y are independently a branched or straight chain $C_1$–$C_8$ alkylene or a branched or straight chain $C_2$–$C_8$ unsaturated alkylene;

R and R" are independently a cycloalkyl group of at least 5 carbon atoms, a carbocyclic aryl group of at least 6 carbon atoms, aralkyl of at least 6 carbon atoms and containing 1–3 separate or fused rings, or a heterocyclic ring, wherein each of R and R" may be substituted in 1–3 positions, or wherein R and R" may form a bond to give a saturated or unsaturated cyclic ring containing at least 2 carbon atoms exclusive of the amidine carbon atom, wherein said cyclic ring may be substituted with one or more alkyl groups of –6 carbon atoms, carbocyclic aryl groups of at least 6 carbon atoms, cycloalkyl groups of 3–12 carbon atoms, or 1–2 fused aromatic rings; and R' is hydrogen, $C_1$–$C_6$ alkyl, $C_2$–$C_6$ alkenyl, trifluoromethyl, or $C_1$–$C_6$ alkylsulfonyl.

51. The method of claim 50 wherein R and R" may be substituted in 1–3 positions by alkyl having 1–8 carbon atoms, hydroxyalkyl having 1–8 carbon atoms, halo, hydroxy, nitro, azido, cyano, isothiocyanato, amino, lower-alkylamino, di-lower-alkylamino, trifluoromethyl, alkoxy having 1–8 carbon atoms, acyloxy, amido and carbamido.

* * * * *